(12) United States Patent
Rappaport et al.

(10) Patent No.: US 9,993,174 B2
(45) Date of Patent: Jun. 12, 2018

(54) DERIVING INDIVIDUAL THORACIC PARAMETERS OF A SUBJECT

(71) Applicant: Sensible Medical Innovations Ltd., Kfar Neter (IL)

(72) Inventors: Dan Rappaport, Tel-Aviv (IL); Nizan Horesh, Caesarea (IL); Ori Hay, Moshav Aviel (IL); Amir Saroka, Tel-Aviv (IL); Daniel Reisfeld, Tel-Aviv (IL); Oren Kalisman, Tel-Aviv (IL); Shlomi Bergida, Udim (IL); Yiftach Barash, Tel-Aviv (IL)

(73) Assignee: Sensible Medical Innovations Ltd., Kfar Neter (IL)

( * ) Notice: Subject to any disclaimer, the term of this patent is extended or adjusted under 35 U.S.C. 154(b) by 154 days.

(21) Appl. No.: 14/374,241

(22) PCT Filed: Jan. 29, 2013

(86) PCT No.: PCT/IL2013/050078
§ 371 (c)(1),
(2) Date: Jul. 24, 2014

(87) PCT Pub. No.: WO2013/111141
PCT Pub. Date: Aug. 1, 2013

(65) Prior Publication Data
US 2015/0031979 A1  Jan. 29, 2015

Related U.S. Application Data

(60) Provisional application No. 61/591,915, filed on Jan. 29, 2012.

(51) Int. Cl.
*A61B 5/05* (2006.01)
*A61B 5/08* (2006.01)
(Continued)

(52) U.S. Cl.
CPC .............. *A61B 5/05* (2013.01); *A61B 5/0044* (2013.01); *A61B 5/0806* (2013.01); *A61B 5/087* (2013.01);
(Continued)

(58) Field of Classification Search
CPC ....... A61B 5/0044; A61B 5/05; A61B 5/0806; A61B 5/0809; A61B 5/0816; A61B 5/087;
(Continued)

(56) References Cited

U.S. PATENT DOCUMENTS

| | | | |
|---|---|---|---|
| 6,106,481 A * | 8/2000 | Cohen | A61B 5/091 128/898 |
| 2003/0040675 A1* | 2/2003 | Sharrock | A61B 5/02007 600/490 |

(Continued)

FOREIGN PATENT DOCUMENTS

| | | |
|---|---|---|
| CN | 101605496 | 12/2009 |
| CN | 102014737 | 4/2011 |

(Continued)

OTHER PUBLICATIONS

Notification of Office Action and Search Report dated Dec. 3, 2015 From the State Intellectual Property Office of the People's Republic of China Re. Application No. 201380006801.2.
(Continued)

*Primary Examiner* — Katherine Fernandez

(57) ABSTRACT

A method of deriving one or more individual thoracic parameters of a subject. The method comprises instructing a subject to perform a thoracic volume manipulation, receiving a plurality of measurements of a plurality of EM signals from a thoracic intrabody area of lungs of the subject during the thoracic volume manipulation, deriving a plurality of thoracic volume values at a plurality of different intervals
(Continued)

during the thoracic volume manipulation so that each the thoracic volume value correspond with another of a plurality of estimated thoracic volumes achieved during the thoracic volume manipulation, and calculating at least one individual thoracic parameter of the subject by combining between the plurality of measurements and the plurality of thoracic volume values.

17 Claims, 9 Drawing Sheets

(51) Int. Cl.
    *A61B 5/087*     (2006.01)
    *A61B 5/00*     (2006.01)
    *A61B 5/091*     (2006.01)

(52) U.S. Cl.
    CPC .......... *A61B 5/0809* (2013.01); *A61B 5/0816* (2013.01); *A61B 5/091* (2013.01); *A61B 5/4872* (2013.01); *A61B 5/4878* (2013.01); *A61B 5/7278* (2013.01)

(58) Field of Classification Search
    CPC ..... A61B 5/091; A61B 5/4872; A61B 5/4878; A61B 5/7278
    See application file for complete search history.

(56) References Cited

U.S. PATENT DOCUMENTS

| 2004/0006279 | A1 | 1/2004 | Arad | |
|---|---|---|---|---|
| 2010/0152600 | A1* | 6/2010 | Droitcour | A61B 5/05 600/534 |
| 2010/0256462 | A1* | 10/2010 | Rappaport | A61B 5/00 600/301 |
| 2011/0060215 | A1* | 3/2011 | Tupin, Jr. | A61B 5/0507 600/425 |

FOREIGN PATENT DOCUMENTS

| JP | 2010-537767 | 12/2010 |
|---|---|---|
| WO | WO 2009/031149 | 3/2009 |
| WO | WO 2013/111141 | 8/2013 |

OTHER PUBLICATIONS

Translation Dated Dec. 21, 2015 of Notification of Office Action dated Dec. 3, 2015 From the State Intellectual Property Office of the People's Republic of China Re. Application No. 201380006801.2.
International Search Report and the Written Opinion dated Jun. 5, 2013 From the International Searching Authority Re. Application No. PCT/ IL2013/050078.
Massagram et al. "Microwave Non-Invasive Sensing of Respiratory Tidal Volume", Proceedings of the 31st Annual International Conference of the IEEE Engineering in Mediicine and Biology Society, IEEE EMBS, Minneapolis, Minnesota, USA, Sep. 2-6, 2009, XP031881217, p. 4832-4835, Sep. 3, 2009. p. 4832, r-h Col., Para 2, p. 4833, r-h Col., Para 3, p. 4835, r-h Col. Para 1, Fig. 1-6.
International Preliminary Report on Patentability dated Aug. 7, 2014 From the International Bureau of WIPO Re. Application No. PCT/ IL2013/050078.
Notice of Reasons for Rejection dated Dec. 13, 2016 From the Japan Patent Office Re. Application No. 2014-553858 and Its Translation Into English. (12 Pages).
Notification of Office Action dated Sep. 13, 2016 From the State Intellectual Property Office of the People's Republic of China Re. Application No. 201380006801.2. (3 Pages).
Notification of Office Action dated Mar. 20, 2017 From the State Intellectual Property Office of the People's Republic of China Re. Application No. 201380006801.2. (4 Pages).
Translation of Notification of Office Action dated Mar. 20, 2017 From the State Intellectual Property Office of the People's Republic of China Re. Application No. 201380006801.2. (3 Pages).
Decision of Rejection dated Aug. 29, 2017 From the Japan Patent Office Re. Application No. 2014-553858 and Its Translation Into English. (10 Pages).

* cited by examiner

DERIVING INDIVIDUAL THORACIC PARAMETERS OF A SUBJECT

RELATED APPLICATIONS

This application is a National Phase of PCT Patent Application No. PCT/IL2013/050078 having International filing date of Jan. 29, 2013, which claims the benefit of priority under 35 USC § 119(e) of U.S. Provisional Patent Application No. 61/591,915, filed on Jan. 29, 2012. The contents of the above applications are all incorporated by reference as if fully set forth herein in their entirety.

FIELD AND BACKGROUND OF THE INVENTION

The present invention, in some embodiments thereof, relates to EM signal analysis and, more particularly, but not exclusively, to EM signal analysis devices for monitoring of thoracic biological properties.

Medical instruments in which an echo of a pulse of EM radiation is used to detect and locate structures in the human body are known, see YOUNG, J. D et. al.

Examination of video pulse radar systems as potential biological exploratory tools in LARSEN, L. E., and JACOBI, J. H. (Eds.): 'Medical applications of microwave imaging' (IEEE Press, New York, 1986), pp. 82-105, which is incorporated herein by reference. Such medical instruments includes microwave imaging devices, which may be referred to as tissue sensing adaptive radar (TSAR) or imaging and other medical devices for detecting and possibly imaging internal biological tissues. The use of electromagnetic waves eliminates the need to expose the tissues to ionizing radiation, as performed during X-ray imaging, and to obtain relatively large tissue contrasts according to their water content.

During the last years, various methods and devices have been developed for diagnosing intrabody tissues of patients using EM radiation. For example, International Patent Application Number IL2008/001198, filed on Sep. 4, 2008, which is incorporated herein by reference, describes a wearable monitoring device for monitoring at least one biological parameter of an internal tissue of an ambulatory user. The wearable monitoring device comprises at least one transducer configured for EM radiation to the internal tissue and intercepting reflections of the EM radiation therefrom in a plurality of continuous or intermittent EM radiation sessions during at least 24 hours, a processing unit configured for analyzing respective reflections and identifying a change in the at least one biological parameter accordingly, a reporting unit configured for generating a report according to the change, and a housing for containing the at least one transducer, the reporting unit, and the processing unit, the housing being configured for being disposed on the body of the ambulatory user.

Using EM radar for cardiac biomechanics assessment is mentioned in E. M. Staderini, "UWB radars in medicine", IEEE Aerospace and Electronic Systems Magazine, vol. 17, no. 1, pp. 13-18, 2002, which the content thereof is incorporated herein by reference.

SUMMARY OF THE INVENTION

According to some embodiments of the present invention, there is provided a device of deriving one or more individual thoracic parameters of a subject. The device comprises a processor, a first interface for receiving a plurality of measurements of EM signals from a thoracic intrabody area of lungs of a subject, wherein each of the plurality of measurements of EM signals reflects a different time point during a thoracic volume manipulation of the subject, a second interface for receiving a plurality of thoracic volume values, wherein each of the plurality of thoracic volume values reflects a different time point during a thoracic volume manipulation of the subject, and an individual thoracic parameter module which uses the processor to calculate at least one individual thoracic parameter using the plurality of EM measurements and the plurality of thoracic volume values.

Optionally, the first interface is associated with a probe having at least one antenna for capturing a plurality of later EM measurements from a subject and a thoracic analysis unit module which monitors thoracic fluid by an analysis of the plurality of later EM measurements in combination with the at least one individual thoracic parameter.

Optionally, the second interface is associated with an instrument for measuring at least one of a breathing airflow of the subject for receiving the plurality of thoracic volume values.

More optionally, the instrument has a chamber with a single airflow opening to allow the subject to blow therethrough during the thoracic volume manipulation.

Optionally, the processor is associated with a presentation unit which presents instructions indicative of how to perform the thoracic volume manipulation in a correlated manner with the measurement of the plurality of thoracic volume values.

Optionally, a memory for storing information relating to the at least one individual thoracic parameter.

Optionally, a processing unit configured to derive one or more clinical parameters according to the at least one individual thoracic parameter and data relating to electromagnetic (EM) radiation received from an internal tissue of the subject.

According to some embodiments of the present invention, there is provided a method of deriving one or more individual thoracic parameters of a subject. The method comprises receiving a plurality of EM measurements of a plurality of EM signals from a thoracic intrabody area of lungs of a subject performing at least one thoracic volume manipulation, deriving a plurality of thoracic volume values corresponding to a plurality of the plurality of EM measurements, and deriving at least one individual thoracic parameter of the subject using the plurality of EM measurements and the plurality of thoracic volume values.

Optionally, the deriving a plurality of thoracic volume values comprises determining a breathing value of the subject in a plurality of separate instances during the thoracic volume manipulation.

Optionally, the plurality of thoracic volume values comprise at least breathing value of the subject.

Optionally, the plurality of EM measurements are received from a thoracic monitoring device monitoring the lungs; and the method comprises calibrating a thoracic analysis device using at least one of the at least one individual thoracic parameter.

Optionally, information relating to the at least one individual thoracic parameter is stored during a calibration session of a thoracic analysis device and is used for analyzing a plurality of later EM measurements which are measured during a monitoring session of the thoracic monitoring device.

More optionally, the calibrating comprises updating a dielectric model of a thorax according to the individual thoracic parameters.

More optionally, the dielectric model is modeled with a plurality of stacked layers having different dielectric properties and selected from a group consisting of skin, fat, muscle, bone, connective tissue and lung.

Optionally, the at least one individual thoracic parameter comprises a member of a group consisting of: heart dimension(s), heart position, fat layer dimensions, thoracic muscle dimension(s), thoracic rib dimension(s), thoracic rib position, lung volume, lung dimension(s), and thorax dimension(s).

Optionally, the at least one individual thoracic parameter comprises dielectric related properties of at least one of a thoracic tissue and a thoracic organ of the subject.

Optionally, the at least one individual thoracic parameter is used in combination with at least one EM measurement to derive at least one clinical parameter of the subject.

Optionally, the plurality of EM signals pass through the lungs.

More optionally, the plurality of EM signals are reflected from at least one object within the thorax of the subject and pass through the lungs.

Optionally, the plurality of EM signals are reflected from the lungs.

Optionally, the plurality of EM signals comprise a plurality of EM signals having a plurality of different frequencies.

Optionally, further comprising presenting to the subject instructions indicative of how to perform the thoracic volume manipulation.

More optionally, the method further comprises presenting to the subject breathing instructions for the subject to perform during the thoracic volume manipulation.

Optionally, the thoracic volume manipulation comprises at least one exhalation and at least one inhalation and performed by the subject.

Optionally, the deriving at least one individual thoracic parameter is performed according to one or more demographic parameters relating to the subject.

Optionally, the thoracic volume manipulation is a member of a group consisting of a Valsalva maneuver and a Miller maneuver.

Optionally, the thoracic volume manipulation includes performing a change of posture, a change of position, a change of lying angle, a change of posture from sitting to lying, a change of posture from lying to sitting, and a rising of the legs.

Optionally, the deriving at least one individual thoracic parameter is performed according to a measured amplitude ratio between a transmitted signal and a received signal.

More optionally, the at least one clinical parameter comprises one or more breathing parameters.

More optionally, the one or more breathing parameters include a member of a group consisting of breathing rate, breathing volumes, tidal volume, residual volume, functional residual capacity (FRC), total lung volumes and minute ventilation.

More optionally, the at least one clinical parameter comprises a member of a group consisting of fluid and/or gas volume in the thorax and/or lung tissue, percentage of fluid in a lung tissue, parameters indicative of fluid content and/or content change, and/or percentage of fluid change in lung tissue.

Optionally, the deriving at least one individual thoracic parameter comprises calculating a phase shift based on the plurality of EM measurements.

Optionally, the deriving at least one individual thoracic parameter comprises calculating fluid content of the lungs.

Optionally, the deriving at least one individual thoracic parameter comprises calculating a depth of the lungs.

According to some embodiments of the present invention, there is provided a method of EM signal analysis. The method comprises receiving at least one individual thoracic parameter of a subject, receiving a plurality of measurements of EM signals from a thoracic intrabody area of the lungs of the subject, and deriving a clinical parameter of the subject using the individual thoracic parameter.

Optionally, the at least one individual thoracic parameter comprises a ratio between a depth of the lungs and a square root of the volume of the lungs.

Optionally, the at least one individual thoracic parameter comprises a population average value selected according to at least one demographic characteristic of the subject.

Optionally, the analyzing comprises deriving dielectric related properties of the lungs according to the plurality of measurements.

Optionally, the clinical parameter is an indication of lung fluid.

According to some embodiments of the present invention, there is provided a system for monitoring one or more clinical parameters of a subject. The system comprises an interface for receiving data relating to electromagnetic (EM) signals received from an internal tissue of a subject, a memory for storing information relating to one or more individual thoracic parameters of the subject, the at least one individual thoracic parameters being the product of a calculation during a calibration session using a plurality of EM signal measurements taken when the subject undergoes at least one thoracic volume manipulation, and a processing unit configured to derive one or more clinical parameters according to the data and the information.

Optionally, the system further comprises a receiver for intercepting the EM signals.

Optionally, the processing unit is configured to derive one or more clinical parameters according to the data and the information during at least one monitoring session which follows the calibration session.

Optionally, the system comprises a receiver for receiving the electromagnetic (EM) radiation from an internal tissue of a subject and a communication module configured to provide data relating thereto to the interface.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system.

In an exemplary embodiment of the invention, one or more tasks according to exemplary embodiments of method and/or system as described herein are performed by a data processor, such as a computing platform for executing a plurality of instructions.

Optionally, the data processor includes a volatile memory for storing instructions and/or data and/or a non-volatile storage, for example, a magnetic hard-disk and/or removable media, for storing instructions and/or data.

Optionally, a network connection is provided as well. A display and/or a user input device such as a keyboard or mouse are optionally provided as well.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DESCRIPTION OF EMBODIMENTS OF THE INVENTION

Figure 1:
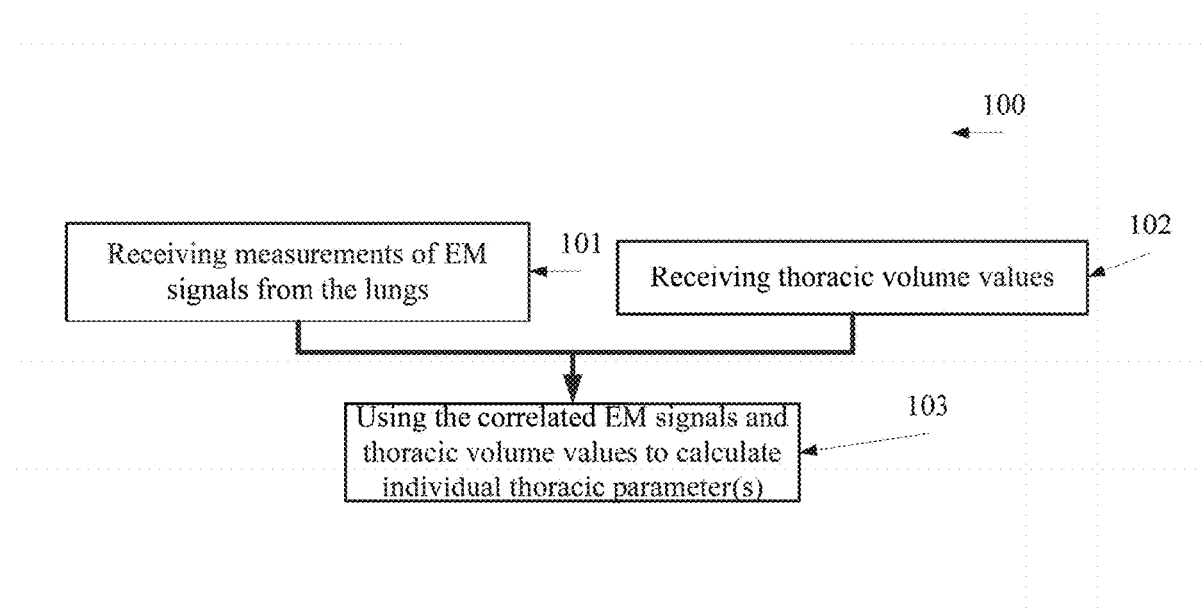
FIG. 1 is a flowchart of a method of deriving individual thoracic parameter(s) of a subject by combining between EM measurements from a thoracic intrabody area and correlated thoracic volume values of the subject's lungs, according to some embodiments of the present invention.

The present invention, in some embodiments thereof, relates to EM signal analysis and, more particularly, but not exclusively, to deriving individual thoracic parameters of a subject, calibrating EM signal analysis devices, and using dielectric thorax models for EM signal analysis.

According to some embodiments of the present invention there are methods, devices and systems for calculating individual thoracic parameters of a subject based on an analysis of measurements of EM signals from the lungs or thorax of the subject and correlated thoracic volume values of the lungs. The measurements and values are optionally captured when the subject undergoes a thoracic volume manipulation. As used herein, a thoracic volume manipulation may include any procedure that affects a thoracic volume value of the subject (e.g. a volume of blood and/or air in the thorax or part thereof) in such manner that the change in volume value may be controlled and/or calculated and/or estimated, directly or indirectly. Some examples for thoracic volume manipulation are detailed herein.

According to some embodiments of the present invention, there are methods and systems of calibrating a thoracic analysis system used for monitoring clinical parameters of a subject, wherein the calibration includes using a thoracic monitoring device to detect EM signals from a thoracic area of lungs, using an individual thoracic parameter(s) deriving device to extract individual thoracic parameters of the subject, for example as outlined above and described below, and analysis of measurements of EM signals from the lungs and/or thorax of the subject may then be performed in a monitoring session according to individual thoracic parameters, optionally using a thoracic analysis device. The individual thoracic parameters may be recalculated from time to time, for example periodically, upon initiation, positioning, and/or relocation of the thoracic monitoring device, and/or the like.

According to some embodiments of the present invention, there are methods and systems of personalizing a dielectric model of the thorax according to individual thoracic parameters which, are related to the specific subject. The personalized dielectric model may be used for calibrating thoracic analysis devices which are used for monitoring one or more clinical parameters of the subject.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Reference is now made to FIG. 1, which is a flowchart 100 of a method of deriving one or more individual thoracic parameters of a subject by using EM measurements from a thoracic intrabody area of the lungs and correlated (for example concurrent) thoracic volume values of her lungs, according to some embodiments of the present invention. The one or more individual thoracic parameters, which have a direct or indirect measurable effect on the propagation of EM signals through the subject's body, may be used for personalizing, for example personalizing a model that is used for EM signals, and/or calibrating one or more thoracic tissue measurements and/or diagnostic devices, for brevity referred to herein as thoracic analysis devices.

The one or more individual thoracic parameters may be or include or be derived from or indicative of or otherwise represent parameters of a subject's thorax that are, or are affected by, one or more of the subject's heart dimensions, heart position, fat layer size, muscle and rib dimensions, lung volume, lung dimensions, thorax dimensions, thoracic dimensions including antero-posterior depth dimensions, lateral width dimensions and/or the like, breathing characteristics, for example functional residual volume of the lung and/or the like. The individual thoracic parameters may include or be derived from or indicative of or otherwise represent dielectric related properties of one or more of the tissues and/or organs of the thorax of the subject. For example, the individual thoracic parameters may be or include parameters of a dielectric model of the thorax of the subject and/or a model that maps changes of dielectric related properties of the lungs when physiological and/or pathophysiological processes occur, for example the process of breathing.

The individual thoracic parameters may be extracted as part of a preliminary session for calibrating the thoracic analysis device, and/or a repetitive process which continuously, randomly and/or iteratively adapts the thoracic analysis device and/or the like. The method may be implemented independently to extract individual thoracic parameter(s) without using imaging modalities.

As used herein, EM measurements, also referred to as measurements, may be measurements of EM radiation and/or signal that is used for monitoring a thoracic tissue parameter, for example fluid level, for example as described in international patent publication number WO2009/031149 and/or international patent publication number WO2009/031150, which are incorporated herein by reference and referred to as the international patent publications. The measurements of EM radiation may be performed in one or more monitoring sessions by any thoracic monitoring device which monitors a thorax and is attached and/or in proximity to the thorax. The EM measurements may be of EM radiation, such as a single EM beam, induced into the thorax and/or received therefrom by the thoracic monitoring device, and is a narrow bandwidth signal, although other acquisition regimes are possible such as wide bandwidth signals.

As used herein, thoracic volume values may include one or more of breathing values such as tidal volume, air volume (e.g. at one or more points in time), functional residual capacity, minute ventilation, lung volumes, thorax and lung dimensions (e.g. at one or more points in time), and breathing rates.

A thoracic analysis system may comprise a thoracic analysis device which uses measurements of EM signals to monitor and/or assess and/or provides clinical parameters related to the state of pathologic and/or disease conditions related to the thoracic tissues and/or organs, for example conditions such as heart failure (HF), acute respiratory distress syndrome (ARDS), acute lung injury (ALI), chronic obstructive pulmonary disease (COPD), pneumonitis, pleural effusion, oncologic diseases, post-operative edema, pneumothorax, and/or for monitoring the subject's response to treatment of these or other disease conditions. The system may be used for finding dielectric related properties indicating the amount of fluids, such as water, blood, and/or inflammation fluids in the monitored internal tissue and/or organ, for example, in the pulmonary tissues of the subject. The system may be associated with, or comprise (e.g. as a single combined device), a thoracic monitoring device that receives EM signals from the subject's thorax, where these signals may be used for said analysis and monitoring. As used herein, receiving measurement of EM signals or receiving of EM signals may include receiving data indicative of said signals and/or derived from said signals in any form, including for example a mathematical representation and/or derivation from the measurements.

As used herein, a dielectric related property of a specific volume describes its interaction with EM fields; it is represented by a frequency dependent complex number describing the electrical permittivity and the conductivity of the volume, as known in the art. It includes the magnetic permeability, and/or electric permittivity and/or conductivity of the composite of materials within a specific volume. Such a dielectric related property may be affected by a presence or distribution of fluid, concentration of substances, such as salts, glucose, in the fluid in the internal tissue and/or organ, the ratio of fibrotic tissue, a concentration of inflammatory substance in the fluid in the internal tissue and/or organ and physical configuration of organs or tissues of different properties in the volume measured. Electric properties, dielectric related properties, and dielectric coefficients are used interchangeably in this application, all referring to the electrical and/or magnetic characteristics of a certain volume containing none, one or more materials. The dielectric related properties of a material, derived from the intercepted EM radiation, describe its interaction with the EM fields. Different human tissues are characterized by different dielectric related properties. The dielectric related properties of a pulmonary tissue are affected by the dielectric related properties of each of its components. For example, a pulmonary tissue comprises blood, lung parenchyma and air, and its dielectric related properties are affected by their relative concentrations. The dielectric related properties of a tissue are determined predominantly by its fluid content. For example, a fat tissue, which is of low fluid content, is characterized by a relatively low dielectric coefficient, and a healthy muscle tissue, which is of relatively high fluid content, is characterized by a relatively high dielectric coefficient. The dielectric related properties of a tissue affect the delivered EM radiation which interacts with the tissue. A change in the dielectric related properties of a tissue may be, for example, a change of the attenuation of a delivered EM radiation, a change in the delay caused by the tissue, a change in the phase modulation of interception, and a change in the dispersion of EM radiation in a tissue.

The thoracic analysis device may be a device used for diagnosing, for example assessing clinical parameters such as breathing volumes, such as tidal volume, residual volume, functional residual capacity total lung volumes, and minute ventilation. In some embodiments, such parameters, also referred to herein as breathing parameters, may also provide indication of a medical condition, and may help to decide on a treatment, or treatment adjustment, or treatment change, possibly a preventive treatment in order to prevent the development of symptomatic pulmonary edema and/or other severe medical state in a subject. In certain medical situations, such a preventive treatment may reduce morbidity and mortality rates. The clinical parameters and/or the breathing parameters may be fluid and/or gas volume in thorax and/or lung tissue values, percentage of fluid in a lung tissue, parameters indicative of fluid content and/or content change, and/or percentage of fluid change in lung tissue.

As described above, the method 100 of FIG. 1 may be used for calibration. The calibration performed according to embodiments described herein may allow deriving clinical parameters such as volumetric and/or functional lung parameters in a more accurate manner. Such accurate clinical parameters may be used in the process of diagnosis, tissue and/or organ monitoring and/or performance assessment and/or medical decision aiding procedure. The calibration described herein reduces effects of specific anatomical, physiological and/or biological characteristics that may reduce the accuracy of the estimation of these clinical parameters.

Figure 2:
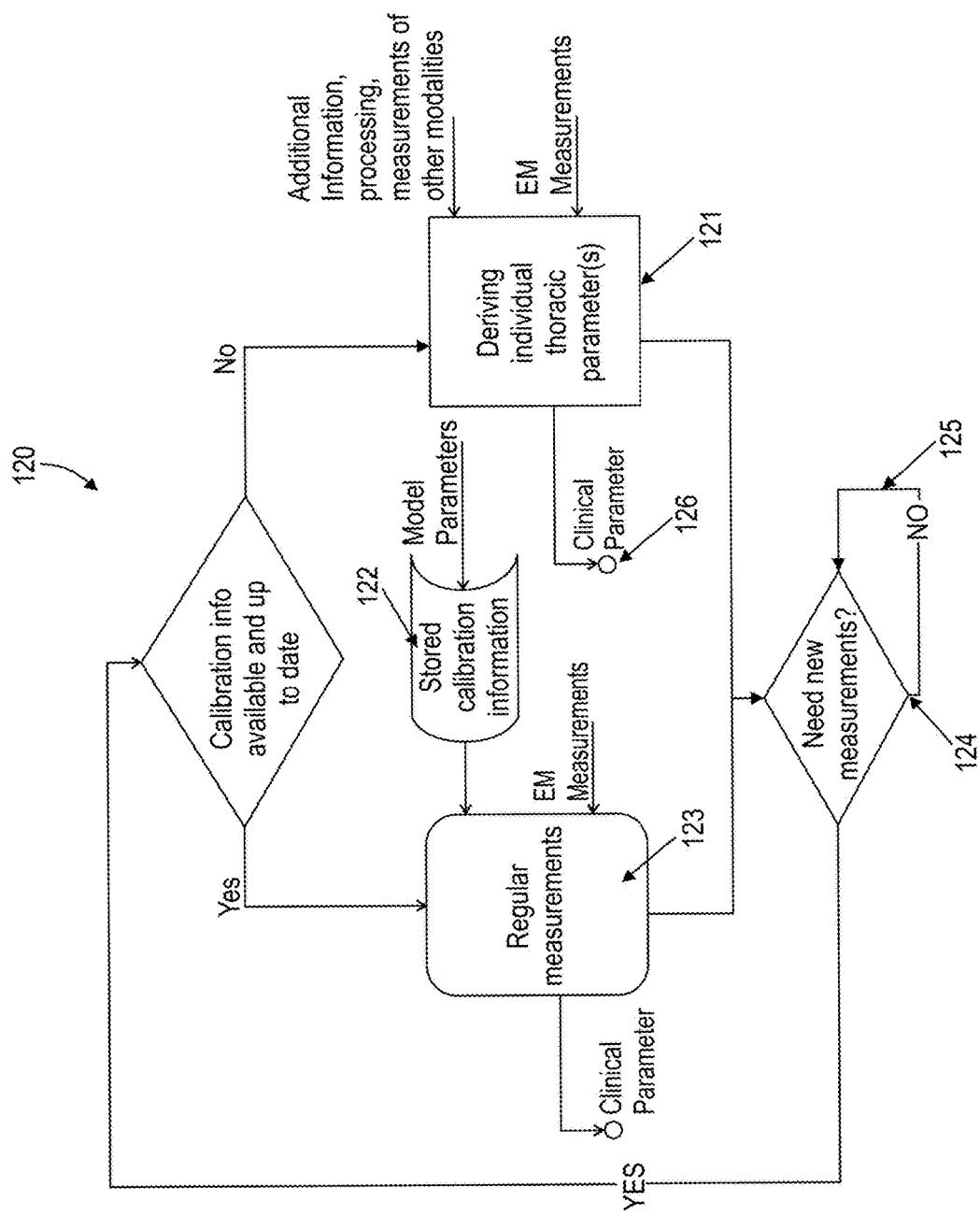
FIG. 2 is a flowchart depicting a process of using a thoracic analysis device for monitoring clinical parameters of a subject based on an analysis of measurements of EM signals from the thorax of a subject where the analysis device is calibrated by using individual thoracic parameters, according to some embodiments of the present invention.

For example, reference is made to FIG. 2, showing a flowchart 120 depicting a process of using a thoracic analysis device for monitoring clinical parameters of a subject based on an analysis of measurements of EM signals from the thorax of a subject where the measurements are calibrated according to individual thoracic parameters or analysis thereof, according to some embodiments of the present invention. As shown at 121, individual thoracic parameters are derived, for example as depicted in FIG. 1 and detailed below. Then, as shown at 122 the individual thoracic parameters or information relating to the individual thoracic parameters (e.g. information indicative of the parameters and/or derived from the individual thoracic parameters), may be stored as calibration data for later use, for example as parameters of a dielectric model.

Optionally, clinical parameters are also derived using the same EM measurements, as shown in 126. Optionally a single device is used to derive individual thoracic parameters and to use them to derive clinical parameters using the same and/or later EM signals.

Now, as shown at 123, operational EM measurements are analyzed using the calibration data to extract clinical parameters, for example, at one or more later measurement sessions. As shown at 124 and 125 whenever a new measurement is done and the calibration is found to be not up to date, for example as it was not acquired for a long time, acquired after more than a certain period in which the thoracic analysis device was used and/or the like, the process depicted in 121-123 is repeated.

Figure 3:
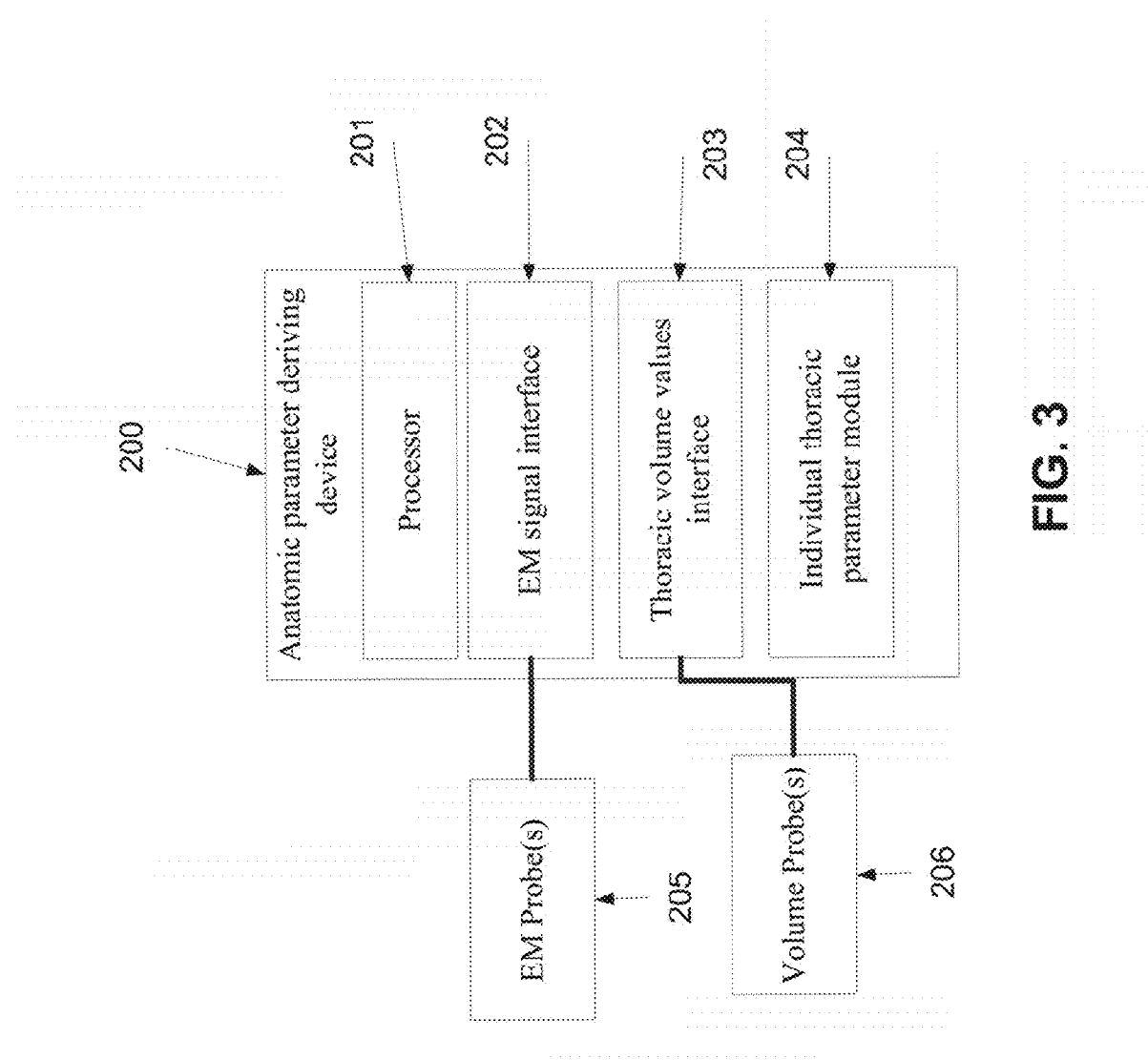
FIG. 3 is a schematic illustration of a system for deriving individual thoracic parameters of a subject, optionally based on the method of FIG. 1, according to some embodiments of the present invention.

Reference is also made to FIG. 3, which is a schematic illustration of a device 200 for deriving individual thoracic parameters of a subject, optionally based on the method of FIG. 1, according to some embodiments of the present invention. The individual thoracic parameter(s) deriving device 200 may be a component of an analysis system for monitoring thoracic fluid or a separate calibration device. The individual thoracic parameter(s) deriving device 200 optionally includes a processor 201, for example a microprocessor, an EM signals interface 202 which receives measurements of EM signals from one or more EM probes 205 that is directed to capture EM signals from a thoracic intrabody area of lungs of a subject. The one or more EM probes 205 may be included with the processor 201 in a single device or be otherwise associated one with the other so as to provide the EM signals interface 202 with measurements of EM signals taken from the one or more EM probes 205. The probe 205 includes one or more transducers each with one or more antenna(s). One or more transducer(s) may be used for transmitting an EM signal beam while other transducer(s) may be used for intercepting the EM signal beam, or the same transducer may be used for capturing the reflected EM signal beam. The EM signals interface 202 may communicate with the transducer(s) via a subject management unit, for example as described in the International Patent Application Number IL2011/000377 filed on May 12, 2011. For example, the EM signal beam passes through lungs, for example from one side to another and/or reflected from an internal object in the body, such as the heart.

As further described below, for deriving of individual thoracic parameters, the EM measurements may be taken at different states of the lungs where in each state the lungs have a different thoracic volume. The different thoracic volumes may be achieved during a thoracic volume manipulation undergone by the subject. The individual thoracic parameter(s) deriving device 200 further includes a thoracic volume value interface 203.

The thoracic volume value interface 203 may receive thoracic volume values from one or more volume probe(s) 206, for example as described below. In such embodiments, thoracic volume value(s) and a measurement(s) of EM signals taken during a common thoracic volume manipulation may be correlated.

Optionally, the individual thoracic parameter(s) deriving device 200 includes an individual thoracic parameter module 204 which uses the processor 201 to derive one or more individual thoracic parameters using the EM signal measurements and correlated thoracic volume values.

In use, as shown at 101 of FIG. 1, measurements of EM signals from a thoracic intrabody area of lungs of the subject are received. The measurements are taken at a set of different thoracic volumes, which are optionally achieved during a thoracic volume manipulation undergone by the subject, for example as described below. The subject may be instructed to perform the thoracic volume manipulation, or the thoracic volume manipulation may be applied to the subject, in correlation with the operation of the individual thoracic parameter(s) deriving device 200.

Optionally, the subject may perform the thoracic volume manipulation while operation of the individual thoracic parameter(s) deriving device 200 is operated in correlation with the subject's performance of manipulation.

Optionally, individual thoracic parameter(s) deriving device 200 operates irrespective of the performance of the thoracic volume manipulation, but data and/or information are analyzed in correlation with the performance of the thoracic volume manipulation.

In addition, as shown at 102 of FIG. 1, thoracic volume values, for example thoracic fluid and/or air volume values, are received. The thoracic volume values are taken during the set of different thoracic volumes which are optionally achieved during the thoracic volume manipulation.

Optionally, the subject is instructed to perform said thoracic volume manipulation in a correlated manner with the deriving of the thoracic volume values. For example, instructions may be presented, for example audibly played and/or visually displayed correlatively with the outputs of the volume probe(s).

Now, as shown at 103, EM measurements and thoracic volume values are used to calculate one or more individual thoracic parameters at each one of the different thoracic volumes by combining between respective correlated EM measurements and thoracic volume values.

During the interception of EM signals, the depth of the lung (D) or the thickness of some of the layers may change, for instance as an outcome of a thoracic volume manipulation, for example the subject's breathing.

Optionally, in order to calibrate a thoracic analysis device, for example to reduce or limit the effect of bodily movements of the chest during the measurement of the EM measurements, for example movements associated with the breathing process and/or other movements, movements are measured and modeled. For example, an electromechanical device in a form of a strap may be placed around the chest of the subject to provide real-time continuous measurements of thoracic volume values, for example the subject's chest circumference, and or in other forms to provide a measurement of the depth of the thorax (front to back), while s/he is measured by the thoracic monitoring device the measurements of EM signals taken by which may be used to monitor thoracic fluid. These measurements may be used to provide corrections to a dielectric lung model. For example, D may be corrected in each measurement by multiplying the change in circumference by a factor.

Additionally or alternatively, the subject may be instructed to perform abdominal breathing to minimize the movement of the rib cage and the expansion of the lung during breathing as a result of the downward expansion of the lungs in such breathing replacing much of the sideward expansion associated with regular breathing. Such breathing may be encouraged by providing the subject with feedback, for example by using the abovementioned electromechanical circumference measurement device, indicating when minimal changes of the chest circumference are detected. Another such option would be to use the circumference measurement device, or tiltmeter devices or accelerometer devices or other such devices in order to follow the movement of the rib cage and select periods of time during which minimal movement are detected.

In order to measure thoracic volume values during a set of different thoracic volumes, the subject is instructed to perform or is subjected to a thoracic volume manipulation, for example by breathing in a certain manner. For example the subject may be instructed to breathe normally for a given time, then in an extreme manner (e.g. deep exhalations and inhalations) for another period of time. These instructions may be implemented using a graphical user interface (GUI) providing a real-time feedback, targets and corrections to the subject in order to achieve a given breathing pattern and/or a characteristic. In another example, the subject is required to inhale or exhale a predefined air volume during the monitoring of the lung, for example while EM signal is received from her lungs. This process may be implemented using an apparatus that measures and/or controls the amount of air that is inhaled and/or exhaled. For example, an air flow meter which measures the amount of inhaled and/or exhaled air, for instance a pneumotach or a spirometer, is used for instructing the subject and identifying thoracic volume values taken during a set of known thoracic volumes. In another example, a bag, a balloon and/or an air container may be used for controlling the inhaling and/or exhaling volume of the subject, where the bag, the balloon and/or the air container has a known capacity and the subject is required to exhale into the balloon until the balloon inflates into a predefined capacity, or where the subject is required to inhale from the balloon until the balloon deflates from its predefined capacity. In another example, a piston like air chamber may be used for measuring and/or controlling air volume inhaled and/or exhaled by the subject, where optionally an indicator on the chamber indicates the volume of air inhaled and/or exhaled. In yet another example, the thoracic volume manipulation includes control and/or measurement of the volume of air in a subject's lungs using an artificial respiration device, for example a ventilator, (for example when the subject is anesthetized, comatose or otherwise incapacitated).

In another example, thoracic volume values are taken during the set of different thoracic volumes which are achieved using an air supply apparatus which supplies air for inhalation, and collects exhaled air in a controlled and or measured quantity. In some embodiments, a mechanical ventilator may be used. Optionally, the air supply apparatus is connected to a monitoring apparatus and measures airflow concurrently with the measurements of EM signals from the lungs of a subject for identifying individual thoracic parameters, optionally for the calibration of the monitoring apparatus.

Figure 4:
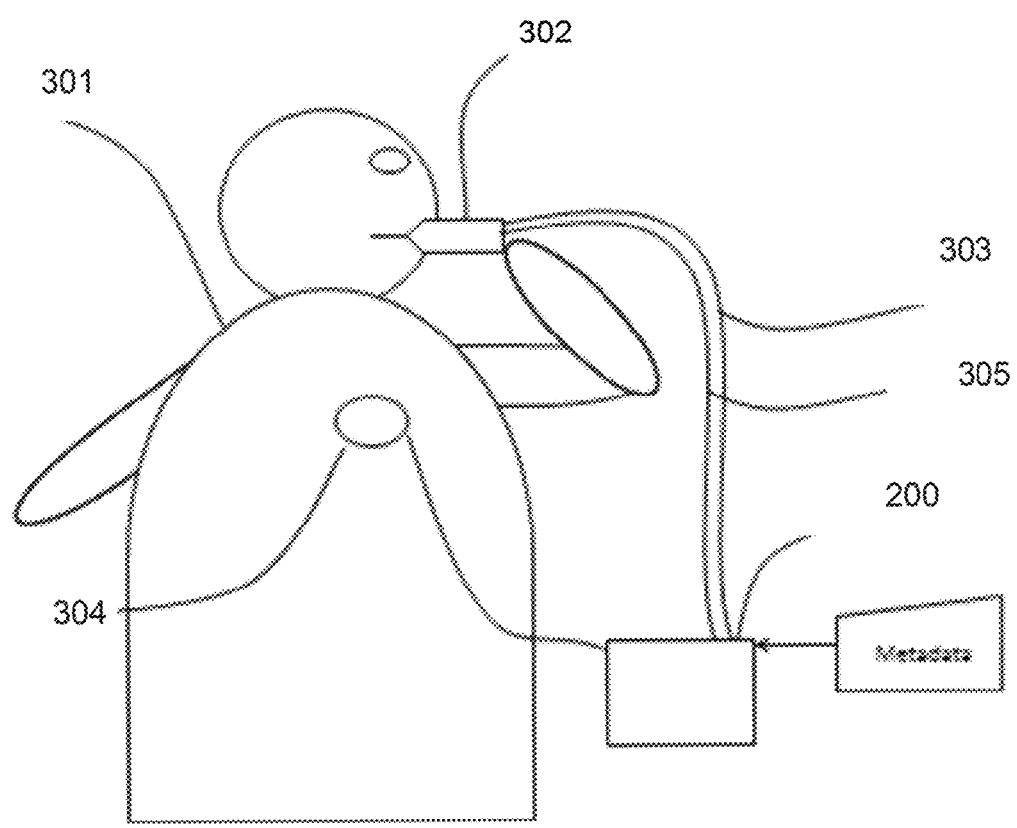
FIG. 4 is a schematic illustration of a subject who exhales and inhales in a controlled manner via an instrument for measuring air flow in association with the individual thoracic parameter(s) deriving system of FIG. 3 that concurrently measures measurements of EM signals from the lungs of the subject, according to some embodiments of the present invention.

For example, FIG. 4 depicts a subject 301 who exhales and inhales in a controlled manner via an instrument for measuring air flow 302, such as a spirometer, while the individual thoracic parameter(s) deriving device 200 concurrently measures EM signals from the lungs using one or more probes 304. The instrument for measuring air flow 302 may be supported by air from a pump, for example via a pump tube 305.

The measurements from the instrument for measuring air flow 302 are forwarded to the individual thoracic parameter(s) deriving device 200 for processing as described herein, for example via a data link 303.

Such controlled or measured changes of air volumes, are indicative of individual thoracic parameters, namely dielectric related properties of the lungs, optionally in a manner that is described in a dielectric thorax model, for example as described below. This allows calibrating the model based measurements.

According to some embodiments of the present invention, metadata is received and used for adjusting the calculated individual thoracic parameters. The metadata may include user generated metadata such as demographic parameters describing the subject, for example age, gender, height, weight, and/or anatomical dimensions. The metadata may include and/or be derived using data measured by mechanical measuring devices, inferred from radiographic images and/or extracted using other means. Using this information the apparatus the individual thoracic parameters may be calculated more accurately.

In some embodiments of the present invention, the individual thoracic parameter(s) deriving device 200 uses one or more body attached sensors to obtain EM measurements while measurements of air quantities, which are inhaled and exhaled by the subject, are provided to the individual thoracic parameter(s) deriving device 200 via a flow meter.

Optionally, a model describing the dielectric properties of the lung at different thoracic volume values is used to generate a set of equations to derive the one or more individual thoracic parameters. In such an embodiment, such a model optionally represents a relationship between dynamic lung content parameters, such as lung air and lung fluid, such as blood, and the individual thoracic parameters optionally in different thoracic volumes.

Optionally, the dielectric model may describe the dielectric related property of the lung as a function of dielectric related properties of air, lung fluids, and lung tissues, and their respective volumes, composition, and/or concentration. For example, the lung of a normal person is composed of approximately 0.5 liter (L) to 0.8 L of blood, approximately 0.5 L of lung tissue, and approximately 1.5-5 L of air, depending on the amount or air inhaled and exhaled in the process of breathing. The overall lung dielectric coefficient may be estimated to be the average of the dielectric coefficients of the three components of air, blood and tissue according to their respective volume and concentration. Another option is to estimate the equivalent dielectric coefficient by averaging a square root of the dielectric coefficients according to a respective volume concentration, and calculating a square of the total. Other dielectric models for estimating the equivalent dielectric coefficient of a mixture exist. Such methods may be used to model the lung and/or other thoracic tissues and/or organs' dielectric properties at different periods along the breathing cycle and for different edema states or other lung changes. For example, at the end of inspiration a model can assume 2 liters of air present in the lungs, and 1.5 liters of air content at the end of expiration.

Reference is now made to a calculation that is based on a dielectric thorax model that assumes an anatomical configuration where a collection of tissues including the lung that makes up a medium traversed by the EM signals. For example, the dielectric thorax model is defined as a chest wall model as described in international patent application number WO2009/031150 filed on Sep. 4, 2008.

Reference is now made to Equations 1-7, which are a mathematical description of an exemplary dielectric thorax model and a process of acquiring individual thoracic parameters which are substituted in the dielectric thorax model for calibration.

Optionally, the model is based on the following assumption:

$$E_{ratio} = \frac{E_r}{E_t} \quad \text{Equation 1}$$

where $$\frac{E_r}{E_t} = f(V, V_{fluid}, V_{air},$$

Dielectric properties of the thoracic tissues,

Anatomical parameters)

where V denotes a total lung tissue volume composed of gas (i.e. air) and lung fluid, $V_{fluid}$ denotes a total volume of fluids in the lung, for example measured in cubic centimeter (CC), where the fluid content comprises a combination of extravascular, intravascular, and intracellular fluid, and $V_{air}$ denotes lung air content in volume units.

$$E_{ratio} = \frac{E_r}{E_t}$$

denotes a ratio between a received (i.e. intercepted; $E_r$) signal and a transmitted (i.e. induced; $E_t$) signal in terms of the electrical component of the EM field.

It should be noted that lung fluid includes tissue contents and fluids including blood.

It should be noted that some embodiments of the present invention are not limited to one model or another and may use various models that describe fluid content of the lung as part of its parameters.

Figure 5A:
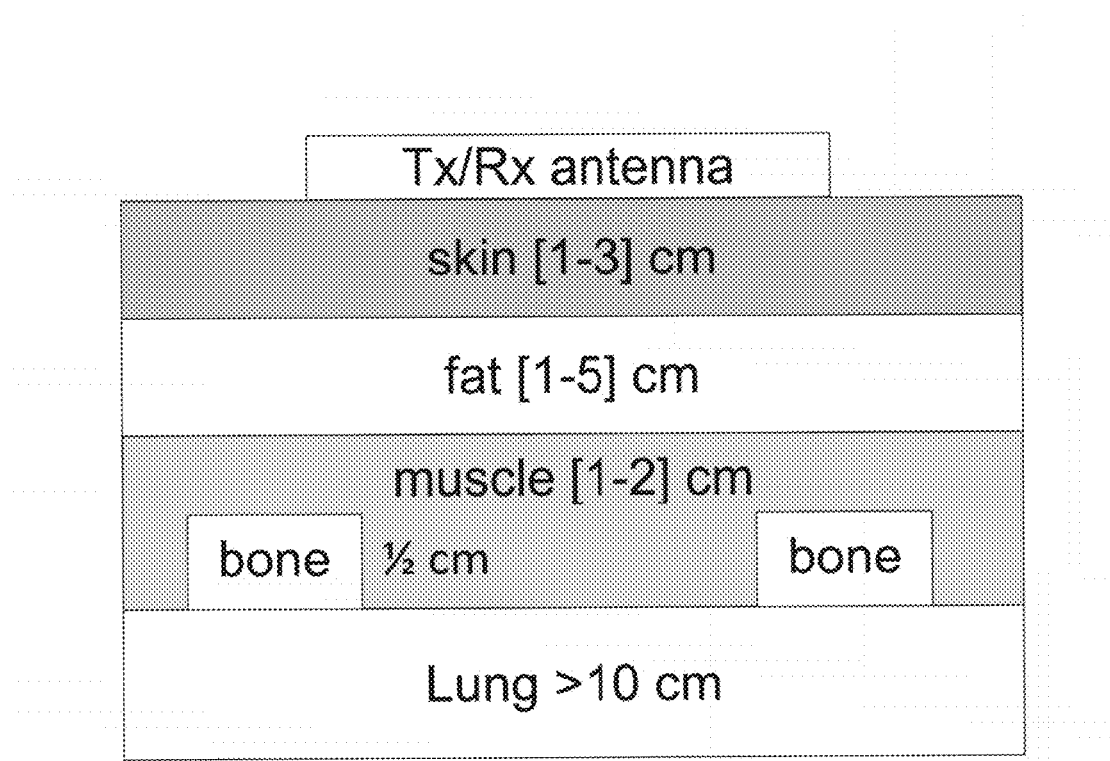
FIG. 5A is a schematic illustration of a multilayer model of the thorax, according to some embodiments of the present invention.
Figure 5B:
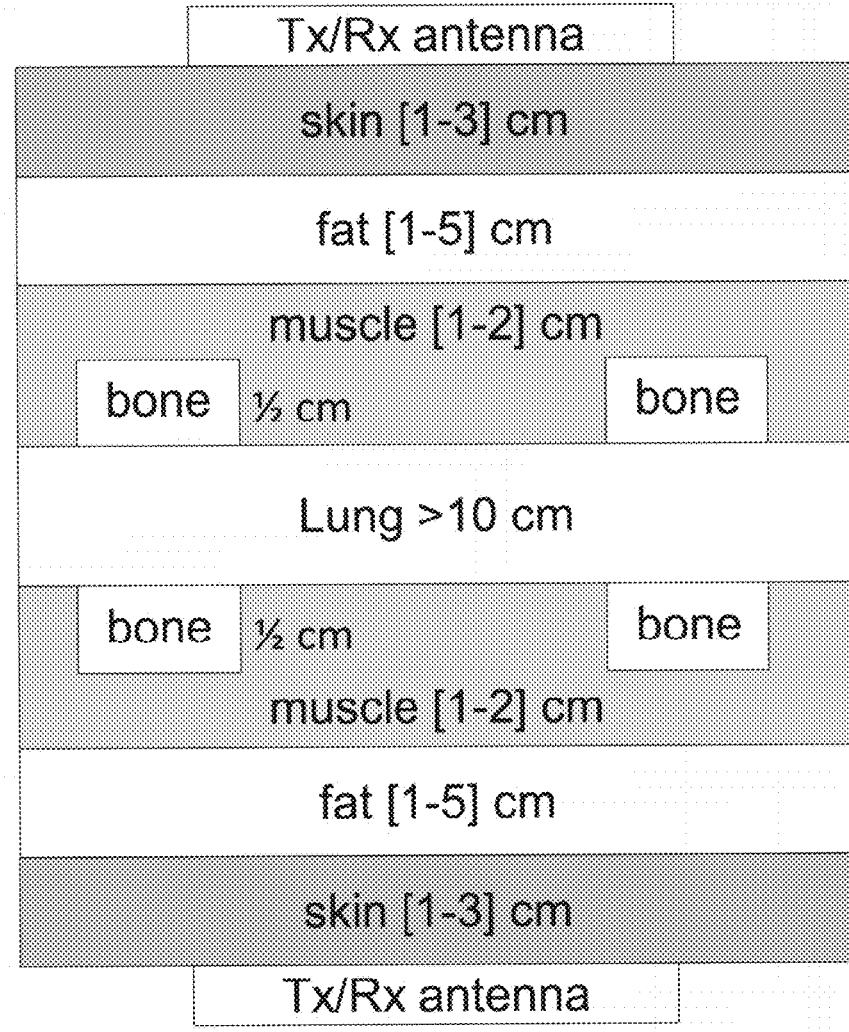
FIG. 5B is a schematic illustration of a multilayer model of the thorax, according to some embodiments of the present invention.

Optionally, the dielectric thorax model is modeled as stacked layers, such as skin, fat, muscle, and lung, where each layer has a different dielectric property, for example as depicted in FIG. 5A. Optionally the reference chest wall model maps expected dielectric coefficients of tissues of an exemplary reference model of EM properties of tissues of a thorax section. For example, the model at FIG. 5A includes the following layers with the following possible thicknesses: a skin tissue layer (1-3 mm), a fat tissue layer (50-500 mm), a muscle tissue layer (50-200 mm), a bone layer (30-60 mm), and a pulmonary tissue layer (~100 mm). Another example is depicted at FIG. 5B which is a side to side model that includes the following layers with the following possible thicknesses: a skin tissue layer (1-3 mm), a fat tissue layer (1-5 cm), a muscle tissue layer (1-2 cm), a bone layer (0.5 cm), a pulmonary tissue layer (~100 mm), a bone layer (0.5 cm) a muscle tissue layer (1-2 cm), a fat tissue layer (1-5 cm), and a skin tissue layer (1-3 mm).

For some or all the layers, the reference chest wall model includes one or more of the following parameters: a relative dielectric coefficient, thickness, for example as described above, an estimated signal shape, and an equivalent frequency response of a layer capturing an effect imposed on an EM signal propagating therethrough, for example an estimation of attenuation and dispersion of a pulse which propagates through the respective layer. Such a model may be presented in phasor notation as:

$$\overline{E_{ratio}} = e^{-j2\pi \frac{f}{c} \cdot \sum_{i \in tissues} D_i \cdot \sqrt{\varepsilon_i + j\varepsilon_i'}} \quad \text{Equation 2}$$

where $\overline{E_{ratio}}$ denotes a measured phasor relationship between a transmitted signal and a received signal representing the electrical components of the electromagnetic radiation at a given frequency, $D_i$ denotes a propagation distance within $i^{th}$ layer (layer thickness) for example skin layer or fat layer, $\in_i$ and $\in_i'$ denote real and imaginary parts of dielectric permittivity (dielectric coefficient) of the $i^{th}$ layer, f denotes a frequency for which the phase shift is calculated, π denotes a Pi constant, and C denotes a speed of light in vacuum constant.

Analysis may now be based on $\varphi = \text{Phase}(\overline{E_{ratio}})$ and/or $\text{Amp} = |\overline{E_{ratio}}|$.

In some embodiments a dielectric thorax model describing a certain phase may be analyzed as follows:

$$\varphi = \sum_{i \in tissues} 2\pi \cdot D_i \cdot \sqrt{\varepsilon_i} \cdot \frac{f}{c} \quad \text{Equation 3}$$

where $\sqrt{\in_i} \approx \text{Re}\sqrt{\in_i + j \cdot \in_i'}$ when the region of interest (ROI) is the lungs, a certain phase may be analyzed as followed:

$$\varphi = \hat{\varphi} + 2\pi \cdot D_{lung} \cdot \sqrt{\varepsilon_{lung}} \cdot \frac{f}{c} \quad \text{Equation 4}$$

where $\hat{\varphi}$ denotes a phase shift is an outcome of all layers other than the lung layer, including phase shift incurred by the one or more EM probes 205 and $D_{lung}$ denotes a length of the lung, defined as the length of the region of lung tissue measured by the apparatus using EM fields, and it is assumed, in this model, a lung dielectric constant per subject in a repeated similar body posture with similar positioning of the one or more EM probes 205, for example transducers.

In some embodiments of the present invention, the lung dielectric constant is determined by a linear material mixture model, for example a material mixture model defined as follows:

$$\varepsilon_{lung} = \frac{V_{air} \cdot \varepsilon_{air} + V_{fluid} \cdot \varepsilon_{fluid}}{V} \quad \text{Equation 5}$$

where when $\epsilon_{air}=1$ and $\epsilon_{fluid}\approx50$, $V_{air}\cdot\epsilon_{air}$ is negligible when compared with $V_{fluid}*\epsilon_{fluid}$. If a frequency of f=3 GHz is selected then Equation 4 equals to:

$$\varphi \cong \hat{\varphi} + 450\cdot D_{lung}\cdot\sqrt{\frac{V_{fluid}}{V}} \quad \text{Equation 6}$$

where $\sqrt{\frac{V_{fluid}}{V}}$ may be referred to as a root fluid concentration (RFC) so that Equation 6 is evident that changes in φ, assuming other model parameters are relatively constant, are linearly correlated with changes in RFC which is an indication of lung fluid changes.

In some embodiments, the use of controlled and/or measured changes in air content enables extraction of other lung fluid indications. As described above, each of a set of thoracic volume values is measured during another of a set of different thoracic volumes which are achieved in a controllable manner.

In some embodiments of the present invention, controlled and/or measured changes in air content enables extraction of individual thoracic parameters. For example, if EM measurements are taken with known quantities of inhaled air with respect to, for example, a deflated volume, for example end of expiration volume, also known as a functional residual capacity (FRC) state of the lung, then using the notation of $$\varphi_i \cong \hat{\varphi} + 450\cdot D_{lung}\cdot\sqrt{\frac{V_{fluid}}{V_{deflated}+\Delta Vi}} \quad \text{Equation 7}$$

which is a six variables equation, that may be solved to obtain parameters $\hat{\varphi}$, $V_{deflated}$, and the term $D_{lung}\cdot\sqrt{V_{fluid}}$, where $V_{deflated}$ denotes a total lung capacity at the end of expiration by substituting known values of inhaled quantities, for example three or more, for instance $\Delta V_1$, $\Delta V_2$ and $\Delta V_3$ and corresponding phase measurements, for instance $\varphi_1$, $\varphi_2$ and $\varphi_3$.

Optionally, in use, the subject is instructed to perform, for example sequentially, a combination of breathing patterns, for example forced exhale pattern, maximal inhale pattern, and normal breathing patterns and the estimated breathing values are used to infer values for $\Delta V_1$, $\Delta V_2$ and $\Delta V_3$.

Obtaining a measurement or estimation of $D_{lung}$ allows calculating $V_{fluid}$. Some examples of how to obtain $D_{lung}$ are herein provided. It should be noted that the acquired individual thoracic parameters may be used for calibration. In such embodiments, the extracted $V_{deflated}$ (i.e. FRC) and $V_{fluid}$ are two individual thoracic parameters which allow deducing another individual thoracic parameter, fluid concentration (FC). For example, FC is calculated as follows:

$$FC = \frac{V_{fluid}}{V_{deflated}} \quad \text{Equation 8}$$

Optionally, the individual thoracic parameters are used for adjusting an analysis of EM measurements obtained while monitoring of intrabody thoracic tissues.

Reference is now made to Equations 9-19, which are a mathematical description of an exemplary dielectric thorax model, a nonlinear mixture model, and a process of acquiring individual thoracic parameters which are substituted in the nonlinear mixture model for calibration. In these embodiments the individual thoracic parameters are dielectric lung constants. Optionally, a nonlinear material mixture model is defined as follows:

$$\sqrt{\varepsilon_{lung}} = \frac{V_{air}\cdot\sqrt{\varepsilon_{air}} + V_{fluid}\cdot\sqrt{\varepsilon_{fluid}}}{V} \quad \text{Equation 9}$$

where if $\epsilon_{air}=1$ and $\epsilon_{fluid}\approx50$, and f=3 GHz then Equation becomes:

$$\varphi \cong \hat{\varphi} + 63\cdot D_{lung}\cdot\frac{V_{air}+V_{fluid}\cdot\sqrt{50}}{V}. \quad \text{Equation 10}$$

In some embodiments of the present invention, controlled and/or measured changes in air content enables extraction of individual thoracic parameters. For example, if EM measurements are taken with known quantities of inhaled air with respect to, for example, a deflated volume, for example end of expiration volume, also known as a FRC state of the lung, then using the notation of:

$$\varphi_i \cong \hat{\varphi} + 63\cdot D_{lung}\cdot\frac{V_{air,deflated}+\Delta Vi+V_{fluid}\cdot\sqrt{50}}{V_{deflated}+\Delta Vi} \quad \text{Equation 11}$$

where $V_{deflated}=V_{air,deflated}+V_{fluid}$ which denotes a total lung capacity at the end of expiration.

In this example, values of inhaled quantities, for example three, for instance $\Delta V_1$, $\Delta V_2$ and $\Delta V_3$ and corresponding phase measurements $\varphi_1$, $\varphi_2$ and $\varphi_3$ may be used to solve and obtain the parameters $\hat{\varphi}$, $V_{deflated}$ and the term $D_{lung}\cdot V_{fluid}$. Similarly to the above, fluid concentration (FC) may be calculated as follows:

$$FC = \frac{V_{fluid}}{V_{deflated}} \quad \text{Equation 12}$$

According to some embodiments of the present invention, relative parameters are extracted; for example, a lung fluid change. The relative measurement may be calculated as follows (taking into account equations 4 and 5):

$$\varphi = \hat{\varphi} + 2\pi f/c\cdot D_{lung}\cdot\sqrt{\frac{V_{air}\cdot\varepsilon_{air}+V_{fluid}\cdot\varepsilon_{fluid}}{V}} \quad \text{Equation 13}$$

where controlled and/or measured changes in air content with respect to, for example, a deflated volume state of the lung may be calculated as follows:

$$\varphi = \quad \text{Equation 14}$$
$$\hat{\varphi} + 2\pi f/c\cdot D_{lung}\cdot\sqrt{\frac{(V_{air,deflated}+\Delta V)\cdot\varepsilon_{air}+V_{fluid}\cdot\varepsilon_{fluid}}{V_{deflated}+\Delta V}}$$

Using a measured or controlled change in $V_{air}$ (i.e. $\Delta V$) and assuming it is small enough, and using a linear approximation, $\Delta \varphi = \text{Const} \cdot (\Delta V)$ where Const may be calculated using a calibration process. Thus, according to the above assumptions, and seeing from the Equations above that $\Delta V$ may be substituted by $(\Delta V_{fluid} \cdot \epsilon_{fluid})$, changes in lung fluid content (i.e. $\Delta V_{fluid}$) may be estimated as follows: $\Delta V_{fluid} = \Delta \varphi / (\text{Const} \cdot \epsilon_{fluid})$.

As described above, the thoracic volume values are taken during the set of different thoracic volumes which are optionally achieved during a thoracic volume manipulation.

According to some embodiments of the present invention, the subject is instructed to perform a Valsalva maneuver and/or Miller maneuver (also known as Muller's maneuver) while electromagnetic waves are measured, optionally using a closed volume chamber apparatus. The subject may, for example, be instructed to exhale normally and from the end of the expiration or the end of inspiration state to perform a Valsalva and/or Miller maneuver. The Valsalva maneuver is performed when the subject exhale against a closed airway, usually when closing his mouth and pinching his nose. The Miller maneuver is performed when the subject inhales against a closed airway, usually closes his mouth and pinches his nose, optionally at the end of expiration. Optionally, the subject is instructed to perform the maneuver for a timed duration. These maneuvers affect pressure in the airways of the lung, and accordingly affect the blood and blood volume in the lungs. Since in the Valsava Maneuver for example a specific blood volume is removed from the lung region due to increased pressure over a time period, this maneuver induces a controlled change in the dielectric properties of the lung. Given a specific pressure that is maintained for a long enough period the lungs reaches an equilibrium in which a specific amount of blood is removed from. For example, when a 40 Millimeter-Quecksilbersäule (mmHg) pressure is applied for 10 second (sec) or more, 200 cc of blood is removed from the lungs and when a 50 mmHg pressure is applied for 10 sec or more, 250 cc of blood is removed. Several pressure levels and corresponding blood fluid removed volumes may be created, see also Dougal Mcclean et al. titled: "Noninvasive Calibration of Cardiac Pressure Transducers in Subjects With Heart Failure: An Aid to Implantable Hemodynamic Monitoring and Therapeutic Guidance", Journal of Cardiac Failure Vol. 12 No. 7 2006.

In this example case, the Valsalva and/or Miller maneuver changes the amount of fluid in the lungs and thus Equation 6 may be set as follows:

$$\varphi \cong \hat{\varphi} + 450 \cdot D_{lung} \cdot \sqrt{\frac{V_{fluid} + \Delta V F_i}{V_{deflated}}} \qquad \text{Equation 15}$$

where $\Delta VF$ denotes an amount of blood fluid removed and/or added by the maneuver. As described above, different parameters for a number of equations may be generated by instructing the subject to perform several maneuvers. Similar to the above, three such equations allow deducing the following individual thoracic parameters: $\hat{\varphi}$, $V_{fluid}$, and a term $D_{lung}/\sqrt{V_{deflated}}$. Obtaining $D_{lung}$ allows calculating $V_{deflated}$. This method may be combined with other methods for creating controlled and/or measured changes in the characteristics of the thorax or the lung and the corresponding model parameters.

Optionally, the subject is instructed to perform a Miller and/or Valsalva maneuver while electromagnetic waves are measured, optionally using a closed volume chamber apparatus.

The Miller maneuver involves forcible inhalation against a closed airway. It may be performed in a similar manner to a Valsalva maneuver with similar results (increasing the amount of blood fluid in the lungs). It may be performed with or without a duration definitions, with or without additional pressure measurement of the intensity and/or control of the negative air pressure; and may be controlled using a similar closed volume chamber apparatus.

Other maneuvers may also be used to change the amount of fluid in the lung in a controlled manner. For example, a change of posture, change of position, a change of lying angle, a change of posture from sitting to lying or vice versa, a raising of the legs in a lying position and/or the like. These maneuvers may be controlled and/or measured to improve accuracy, for example the posture or posture change may be measured and timed, for example using tilt meters, accelerometers, gyroscopes and/or the like. For example, the angle of the torso and/or the angle of the legs may be measured or controlled during the maneuver. Also the duration of the maneuver or its parts may be measured. Also peripheral effects, for example blood pressure, heart rate, respiration rate, may be measured before during or after the maneuver to help in the assessment of the extent of the maneuver and the expected change in the fluid content of the lungs. As with the Valsalva maneuver, a given maneuver creates a new equilibrium state that removes or adds a given amount of fluid to the thorax.

The change, measured in the intercepted EM signal, during the controlled change induced in the subject, may be analyzed, using a dielectric thorax model, to estimate the individual thoracic parameters for the dielectric thorax model. For example, as described above, the individual thoracic parameters may be used to in order to calibrate thoracic analysis device. Therefore, by inducing a controlled change of the dielectric related properties of a monitored lung, for example, while performing EM measurements of the lung, it is possible to track the changes in the received EM signal in view of the induced change. This method may be used to calculate parameters of the model for the subject being monitored using the EM measurements.

These controlled changes may be induced once, several times, periodically, and/or continuously throughout an EM measurement session and/or a monitoring period, in one or more manners, and using one or more degrees of intensity. These controlled changes may include the use of the above methods, and/or other techniques for changing the dielectric related properties of the measured tissue, as mentioned above.

Figure 6:
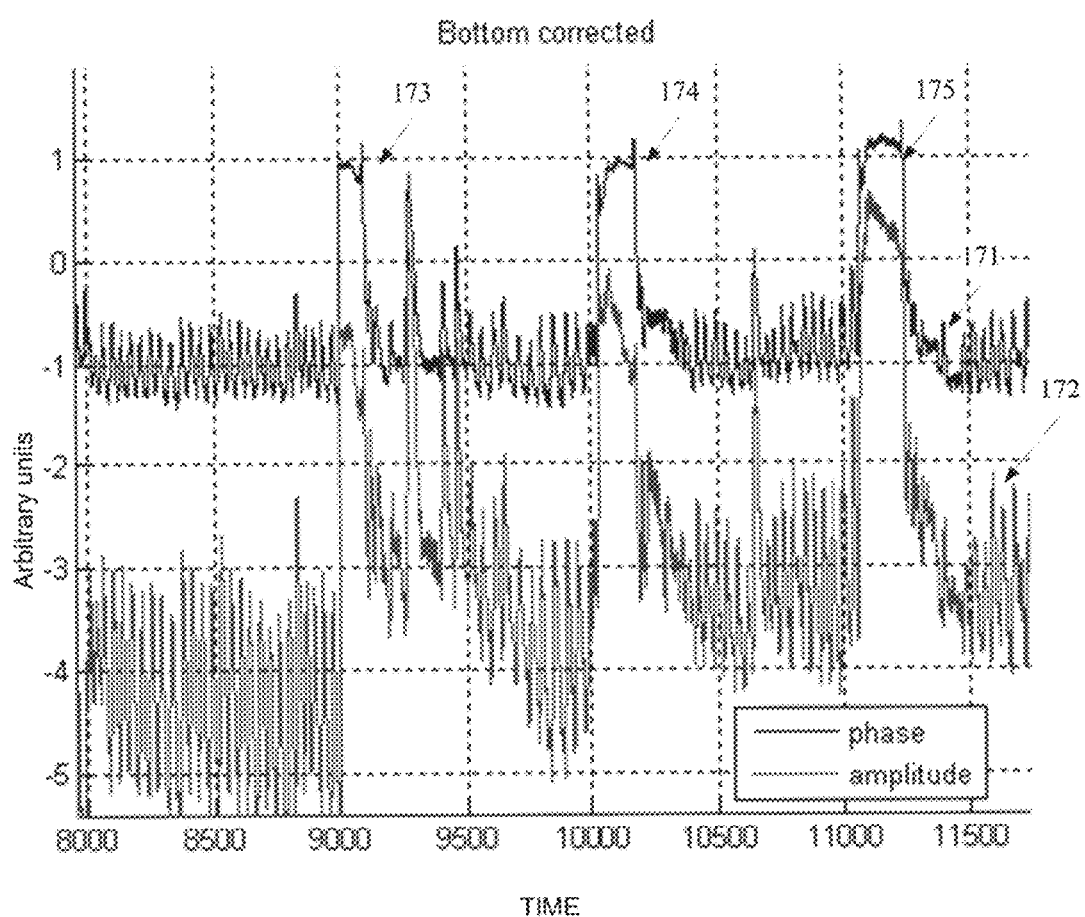
FIG. 6 is a graph depicting amplitude and a phase of an EM measurement signal captured while a subject performed a Valsalva maneuver, according to some embodiments of the present invention.

Optionally, the EM signal is measured while the subject performs the above maneuvers. For example, FIG. 6 depicts phase 171 and amplitude 172 of an EM measurement signal captured while the subject performed a Valsalva maneuver and analyzed over a period of a few minutes and modulated by the breathing of the subject. Three periods where the Valsalva maneuver is performed and a respective removal of a specific volume of blood from the subject's lung are seen at 173-175. EM measurements may be taken during one or more of the maneuvers and/or at a time when the maneuver is not performed.

Figure 7:
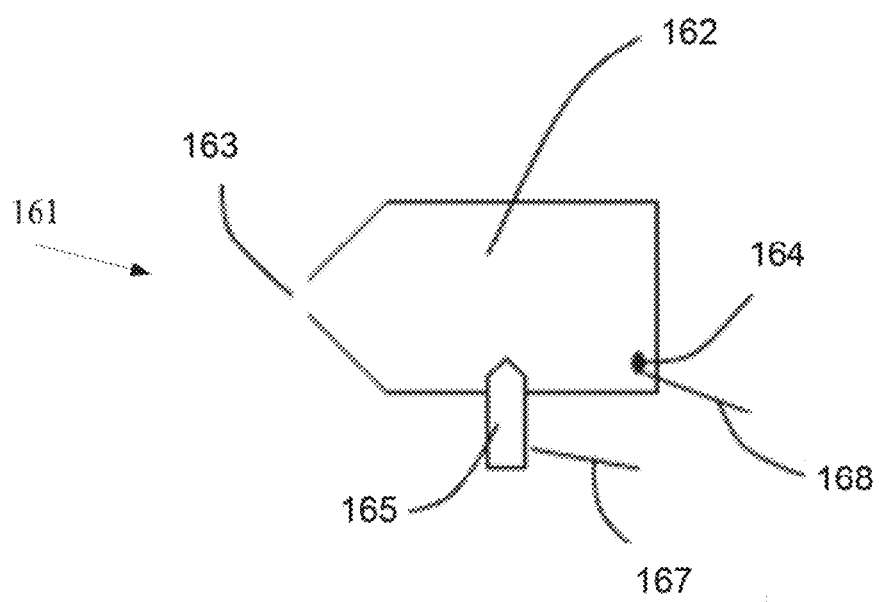
FIG. 7 is a closed volume chamber apparatus, according to some embodiments of the present invention.

According to some embodiments of the present invention, the thoracic volume values are taken during the set of different thoracic volumes which are acquired using a closed volume chamber apparatus, for example the volume chamber apparatus 161 depicted in FIG. 7. The closed volume chamber apparatus 161 indicates air pressure in the lung of the subject over a measured amount of time.

Optionally, the subject is instructed to inhale or to exhale against the closed chamber 162 through a single airflow opening, for example a mouthpiece 163, while the apparatus 161 induces and/or measures air pressure in the chamber 162 using an air pump 165 and/or a pressure sensor 164. The pump 165 and the pressure sensor may be connected with data links 167/8 to an individual thoracic parameter(s) deriving device 200. The apparatus 161 may be controlled by a processing unit that may be embedded in the closed volume chamber apparatus 161. The processing unit may record the pressure measurements, and/or measure the duration that the pressure is maintained and/or control the air pump to create the desired pressure in the chamber. The processing unit may communicate with a subject interface unit to provide information to be used as a basis for instructing the subject to achieve the desired behavior (inhaling or exhaling against the closed chamber to create the desired pressure) for the desired duration.

In use, apparatus 161 may be used to extract the thoracic volume values during a set of identified thoracic volumes.

According to some embodiments of the present invention, the individual thoracic parameters include estimated physiological parameters of the subject. For example, the ratio between the lung's depth (e.g. anteroposterior dimension of the lung) and the square root of the lung volume may also be assumed based on the general population, and/or adjusted based on subject specific characteristics for example weight, height, chest, circumference, and the like.

In another example, tidal volume is assumed to be an average volume, for instance for an adult 500 cubic centimeter (cc) and/or adjusted based on the weight of the subject, for instance assuming a value for a normal individual at rest of 7 milliliter (mL) per kilogram (kg) of body weight and/or in correlation with BMI or fitness level and/or any other subject specific characteristic. The tidal volume may be estimated based on average minute ventilation (defined as the tidal volume multiplied by the respiration rate given as breaths per minute) of, for example, 6 liters per minute and adjusted based on a measured respiration rate, see "Tintalli's Emergency Medicine, Ch. 22"; Todd L. Slesinger, M.D.; 2011. Similarly, respiratory functional residual volume may be estimated as the general population overage of 2500 cc and/or based on weight and age of the subject, for instance (0.0275*Age[years]+0.0189*Height [cm]−2.6139) liters for normal-weight individuals and (0.0277*Age[years]+0.0138*Height[cm]−2.3967) liters for overweight individuals, see MILLER, WAYNE C.; SWENSEN, THOMAS; WALLACE, JANET P. (February 1998). "Derivation of prediction equations for RV in overweight men and women", Medicine & Science in Sports & Exercise 30 (2): 322-327.

According to some embodiments of the present invention, the clinical parameters include breathing parameters such as a breathing rate, minute ventilation, a tidal volume, a residual volume, and/or FRC.

Optionally, the breathing values, used as thoracic volume values, for example the tidal volume, are used for calibrating using an EM probe that captures EM signals from the lungs. Following calibration the EM measurements may be used to continue and provide the tidal volume measurements; and in addition minute ventilation may be provided by using the tidal volume measurement multiplied by a breathing rate value.

The breathing rate value may be assessed using one or more frequency analysis methods applied to the measured EM signal. For example, looking for a maximum power peak in the frequency domain, a representation of the phase of the measured EM signal in a range between 2/60 Hertz (Hz) and 1 Hz, after employing methods for removing the effects heart beating from the signal.

Optionally, residual volume (RV) may be calculated using the above method while the subject exhales as much as she can. In this case, the resulting equation $$\varphi_i \cong \hat{\varphi} + 450 \cdot D_{lung} \cdot \sqrt{\frac{V_{fluid}}{V_{RV} + \Delta V i}}$$

may be used with controlled and/or measured changes in air content to obtain RV.

Breathing parameters are of importance in relation to several pathologies and medical conditions, for example heart failure, chronic obstructive pulmonary disease (COPD), interstitial lung disease (ILD), and/or acute lung injury (ALI).

Optionally, a noise model is generated and used to improve the calculation of the individual thoracic parameters, for example using a least square error method.

According to some embodiments of the present invention, a thoracic analysis device is calibrated based on individual thoracic parameter(s) which are calculated independently from information about current thoracic volumes. For example, the individual thoracic parameter(s) may include a lung diameter that is approximated according to the average in the population estimated at about 17.1 centimeters (cm) or any other appropriate estimated average. This and other approximations may be more accurate if they are estimated based on the subject's general physical parameters, such as height, weight, body mass index (BMI), age, gender and/or fat-muscle ratio. Another option is to approximate lung diameter according to a chest perimeter of the subject.

The chest perimeter may be measured under the armpits of the subject and multiplied by a factor such as 0.164 (or any other appropriate factor).

Optionally, lung diameter is approximated according to chest depth of the subject.

Optionally, the chest (i.e. depth front to back) may be measured using a designated mechanical tool. The measuring is optionally correlated with phase shift measuring and optionally multiplied by a factor.

Another example of independently calculated individual thoracic parameter(s) are individual thoracic parameters measured using an imaging modality, such as computerized tomography (CT), magnetic resonance imaging (MRI), ultrasound imaging, and/or radiographic, and/or other imaging methods or any other known system for finding the lung width along the measurement path. For example, dielectric related properties of the tissues in the thorax, and specifically in regions of interest may be estimated.

For example, fluid to air ratio of the lung tissue, fat tissue and/or other tissues may be estimated based on the analysis of image gray levels in regions of interest in a CT image, or other imaging modalities. Such an analysis of a CT image to assess lung fluid concentration may be performed by extracting a three dimensional (3D) region of interest in the image, say within the lung, or the entire lung region; and computing the average attenuation level of the region in Hounsfield units (HU). $HU_i$ may be converted into fluid concentration (i.e. the ratio of the volume of blood, parenchyma and any pathological fluid to the total volume) using a linear scale. Transformation from HU to fluid concentration percentage may be performed by assigning a value between 0% and 100% along the range of HU values, between 1000 HU (the calibrated radiodensity of air) and 0 HU (the calibrated radiodensity of water), for instance 800 HU is equivalent to 80% air content and 20% fluid concentration.

Another example of independently calculated individual thoracic parameter(s) are individual thoracic parameters measured using EM signal reflected from the thorax, for example the measuring of D as described in Staderini EM, UWB radars in medicine, IEEE Aerospace and Electronic Systems, Volume: 17 (1) 2002.

According to some embodiments of the present invention, breathing values are quantified by processing amplitude of an intercepted signal in relation to a delivered signal and used, in conjunction with a model, such as the above dielectric thorax model, to calculate individual thoracic parameters.

Reference is now made to a model that is defined for narrowband signals passing through the lungs of the subject. This model may be adjusted for other analyses of other signals, for example EM signals which are transmitted and captured from a probe that is attached on the back, the chest, and/or below the arm of the subject. In such embodiments, the model may be defined as follows:

$$Amp = |\overline{E_{ratio}}| = e^{-j2\pi \frac{f}{C} \cdot \Sigma_{i \in tissues} D_i \cdot Im(\sqrt{\varepsilon_i + j \cdot \varepsilon'_i})} \qquad \text{Equation 16}$$

where $Amp = |\overline{E_{ratio}}|$ denotes a measured amplitude ratio between a transmitted signal and a received signal representing an electrical component of the electromagnetic signal.

The following equation, $$\ln(Amp) = \ln(Amp_0) - j2\pi \frac{f}{C} \cdot D_{lung} \cdot Im(\sqrt{\varepsilon_{lung} + j \cdot \varepsilon'_{lung}}) \qquad \text{Equation 17}$$

using the notation $\varepsilon^c = \varepsilon + j \cdot \varepsilon'$, may use a model, such as the one in Equation 5, for example $$\varepsilon^C_{lung} = \frac{V_{air} + V_{fluid} \cdot \varepsilon^c_{fluid}}{V}$$

and similarly to the above description approximate $$\varepsilon^C_{lung} \approx \frac{V_{air} + V_{fluid} \cdot \varepsilon^c_{fluid}}{V}.$$

Using a natural logarithm, the following is received:

$$\ln(Amp) = \qquad \text{Equation 18}$$

$$\ln(Amp_0) - j2\pi \frac{f}{C} \cdot D_{lung} \cdot Im\left(\sqrt{\frac{V_{air} + V_{fluid} \cdot \varepsilon^c_{fluid}}{V}}\right)$$

whereas mentioned in other described embodiments, controlled and/or measured changes in air content ($\Delta v_i$) enable extraction of other individual thoracic parameters. For example, as described above, if several measurements are taken with known quantities of inhaled air ($\Delta v_i$) with respect to, the deflated (i.e. post exhalation) state of the lung, the following is received:

$$\ln(Amp)_i = \ln(Amp_0) - \qquad \text{Equation 19}$$

$$j2\pi \frac{f}{C} \cdot D_{lung} \cdot Im\left(\sqrt{\frac{V_{deflated} + \Delta v_i + V_{fluid} \cdot \varepsilon^c_{fluid}}{V_{deflated} + \Delta v_i + V_{fluid}}}\right)$$

Using the known values of four or more inhaled quantities ($\Delta V_i$) and their corresponding phase measurements $\ln(Amp)_i$ one may solve and obtain the following parameters $\ln(Amp_0)$, $V_{deflated}$, $V_{fluid}$, and $D_{lung}$.

In these embodiments, extracted $V_{deflated}$ and $V_{fluid}$ are two of the individual thoracic parameters of interest.

According to some embodiments of the present invention, the above models share parameters to create a hybrid model that can enhance the accuracy of the results of the estimation of the individual thoracic parameters. Combinations of the models may be implemented as extended sets of equations solved in any of the mentioned methods or others known in the art. In a similar manner, any of the aforementioned models may be combined with one another and/or with other models.

According to some embodiments of the present invention, multiple frequencies may be used by a thoracic monitoring device and/or thoracic analysis device. The above and other possible models may be used with a varied frequency content to obtain an accurate estimation of the parameters in view of measurement errors.

For example, $\varepsilon^c_{fluid}$ given in the above models and assuming a given frequency, has different values at different frequencies. Performing measurements at multiple frequencies creates a plurality of linearly independent sets of equations, allowing more accurate estimations of the individual thoracic parameters. Multiple frequencies measurements may be measured substantially simultaneously to create additional equations with the same air content status of the lung at the same point in time.

Similar thorax models to the ones above may be used with multiple frequencies based thorax analysis devices for modeling effects of individual thoracic parameters and obtaining clinical parameters. Additionally in a similar manner similar methods for deriving individual thoracic parameters using multiple frequencies can be employed.

Optionally, measurements at multiple frequencies are used to overcome one or more phase ambiguity problems, for example $2*P_i$ uncertainty in the measured phase in the presence of measurement noise that may arise when analyzing a phase of a low bandwidth signal. For example, it is possible to estimate a phase group delay of a wideband modulated signal in order to resolve phase ambiguities, and then extract the frequency specific phase shifts to be used in one or more of the above models. For example Equation 19 may be used with simultaneous measurements of multiple frequencies $f_j$ to produce the following set of equations:

$$(f_j)\ln(Amp)_{i,j} = \ln(Amp_0) - \qquad \text{Equation 20}$$

$$j2\pi \frac{f}{C} \cdot D_{lung} \cdot Im\left(\sqrt{\frac{V_{deflated} + \Delta v_i + V_{fluid} \cdot \varepsilon^c(f_j)_{fluid}}{V_{deflated} + \Delta v_i + V_{fluid}}}\right)$$

According to some embodiments of the present invention, EM signals from multiple transducers which are placed in multiple locations (e.g. multiple locations on the subject's thorax) to monitor the subject are separately analyzed.

Optionally, two signal transducers are placed in two different locations used to transmit EM signals between them. However, one or more of them may transmit a signal and measure it's reflection in addition or instead. When more than two transducers are used additional paths may be employed. This may allow, for example, reducing measurement errors. Multiple locations may allow receiving EM signals passing via multiple paths.

Assuming that the paths are in the same general region, fluid content in each path may be assumed to be the same. Thus, for each such path, a different equation may be solved to calculate the individual thoracic parameters of interest. For example, in any of the above models each path is associated with a different $D_{lung}$ parameter. Simultaneous measurements may be used in a single equation system, with more linearly independent equations, that may be used for more robust estimations under certain measurement noise conditions.

As an example, Equation 6 is used with controlled changes in lung air content and simultaneous 2-path measurements to produce the following:

$$\varphi_{i,j} \cong \hat{\varphi} + 150 \cdot D_{lung_j} \cdot \sqrt{\frac{V_{fluid}}{V_{deflated} + \Delta V_i}}, \; j = 1, 2 \quad \text{Equation 21}$$

Optionally, in this example, less than three measurements are used, for example when parameters are from different sources, for instance when the volume of the lungs is received from an external device and/or inputted by the subject and/or any operator.

Optionally, multiple locations and multiple frequencies may be combined to create one or more equation systems that increase robustness of the estimation of the individual thoracic parameters.

Figure 8:
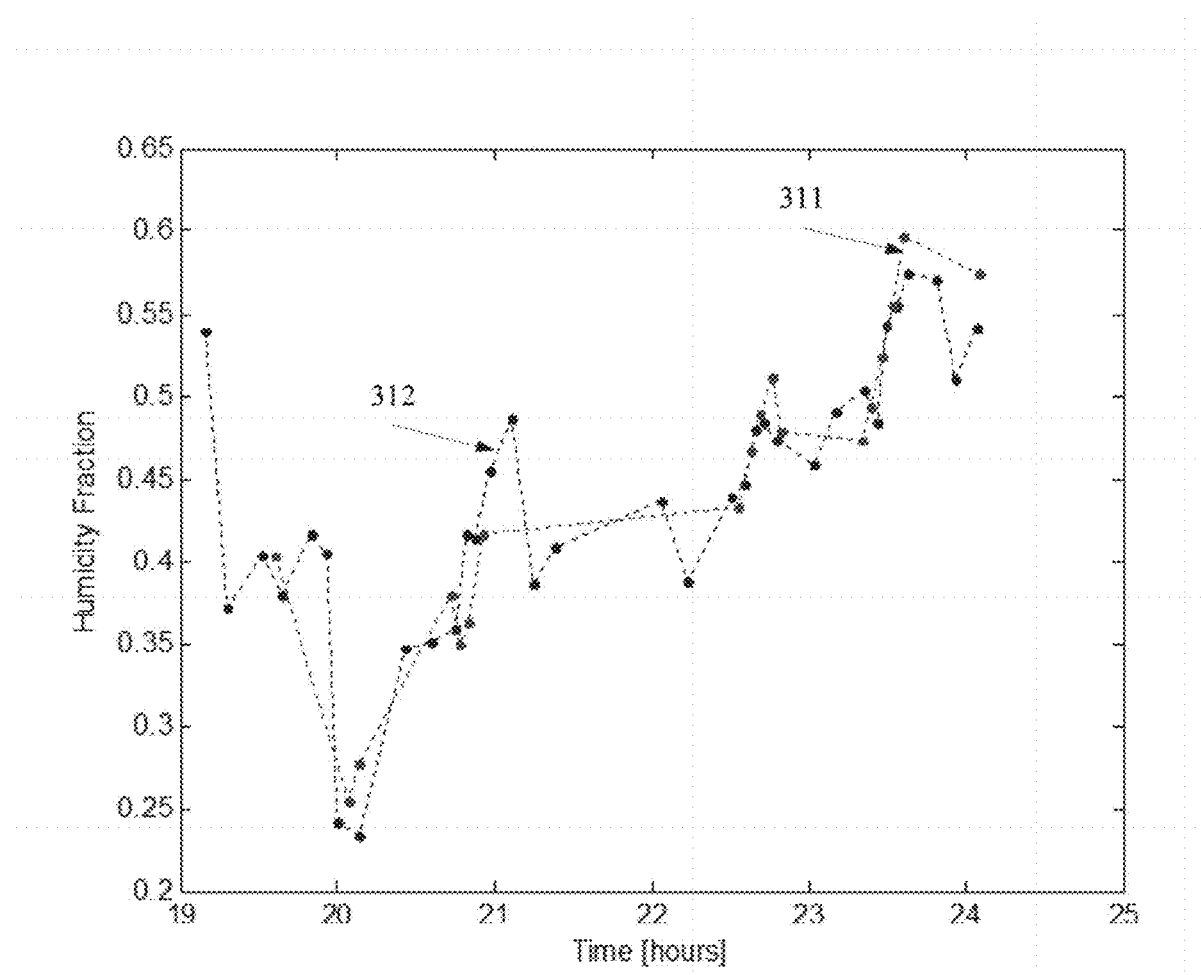
FIG. 8 is an experiment graph reflecting a calculation of lung fluid concentration calculated based on EM measurement of an animal subject, according to some embodiments of the present invention, compared to a computed tomography (CT) based estimation of the same parameter based on multiple images acquired along the course of the experiment.

For example, reference is now made to FIG. 8, which is an experiment graph reflecting a calculation of lung fluid concentration 311 calculated based on EM measurement of an animal subject compared to a CT based estimation 312 of the same parameter based on multiple images acquired along the course of the experiment. The experiment is held concurrently with breathing volume spirometer measurements, and using the above mentioned model describing signal phase and signal amplitude, with a linear mixture model and a mechanical measurement based estimation of D. The graph depicts the fluid concentration, also referred to as fluid content, parameter estimation done multiple times over the course of four hours while the animal lung fluid has changed rapidly using a systemic saline overload experiment protocol.

It should be noted that when the EM signal is a reflected signal, for example when a single transceiver is used or when a receiving element and a transmitting element are mounted on the same side of the subject body (referred to herein as an $S_{11}$ probe), a model that takes into account the back and forth route of the EM wave may be employed. For example, when a wave is reflected between two layers of dielectric media, the coefficient of reflection is as follows:

$$R = \frac{E_R}{E_T} = \frac{\sqrt{\varepsilon_1} - \sqrt{\varepsilon_2}}{\sqrt{\varepsilon_1} + \sqrt{\varepsilon_2}} \quad \text{Equation 22}$$

where $\varepsilon_1$ denotes a dielectric coefficient of the first layer and $\varepsilon_2$ denotes a dielectric coefficient of the second layer.

Thus, the $S_{11}$ coefficient is written as below:

$$S_{11}(V) = R_0 + C \left( \frac{\sqrt{\varepsilon_1} - \sqrt{\varepsilon_{lung}(V)}}{\sqrt{\varepsilon_1} + \sqrt{\varepsilon_{lung}(V)}} \right) \quad \text{Equation 23}$$

where $\varepsilon_1$ denotes a dielectric coefficient of the lung wall, $\varepsilon_{lung}$ denotes a dielectric coefficient of the lung tissue, V denotes a lung volume, and $R_0$, C denotes constants related to other tissue layers which are more proximate to the probe and the properties of the probe. Using the model, for example such as the one described in Equation 8, the following may be written:

$$\sqrt{\varepsilon_{lung}(\Delta V)} = \frac{\sqrt{\varepsilon_{air}}(V_{deflated} - V_{fluid} + \Delta V) + \sqrt{\varepsilon_{fluid}} V_{fluid}}{V_{deflated} + \Delta V} \quad \text{Equation 24}$$

where $V_{deflated}$ denotes a total lung volume at rest (FRV), then $$\sqrt{\varepsilon_{lung}(0)} = \frac{\sqrt{\varepsilon_{air}} V_{air} + \sqrt{\varepsilon_{fluid}} V_{fluid}}{V_{deflated}} \quad \text{Equation 25}$$

The difference between the signals may be estimated to eliminate $R_0$:

$$S_{11}(\Delta V_1) - S_{11}(0) = \quad \text{Equation 26}$$

$$\frac{\sqrt{\varepsilon_1} - \sqrt{\varepsilon_{lung}(\Delta V_1)}}{\sqrt{\varepsilon_1} + \sqrt{\varepsilon_{lung}(\Delta V_1)}} - \frac{\sqrt{\varepsilon_1} - \sqrt{\varepsilon_{lung}(0)}}{\sqrt{\varepsilon_1} + \sqrt{\varepsilon_{lung}(0)}}$$

Furthermore, the quotient of the signals may be evaluated to eliminate C:

$$\frac{S_{11}(\Delta V_1) - S_{11}(0)}{S_{11}(\Delta V_2) - S_{11}(0)} = \quad \text{Equation 27}$$

$$\frac{\frac{\sqrt{\varepsilon_1} - \sqrt{\varepsilon_{lung}(\Delta V_1)}}{\sqrt{\varepsilon_1} + \sqrt{\varepsilon_{lung}(\Delta V_1)}} - \frac{\sqrt{\varepsilon_1} - \sqrt{\varepsilon_{lung}(0)}}{\sqrt{\varepsilon_1} + \sqrt{\varepsilon_{lung}(0)}}}{\frac{\sqrt{\varepsilon_1} - \sqrt{\varepsilon_{lung}(\Delta V_2)}}{\sqrt{\varepsilon_1} + \sqrt{\varepsilon_{lung}(\Delta V_2)}} - \frac{\sqrt{\varepsilon_1} - \sqrt{\varepsilon_{lung}(0)}}{\sqrt{\varepsilon_1} + \sqrt{\varepsilon_{lung}(0)}}}$$

The above is dependent only on $V_{fluid}$, $V_{deflated}$, $\varepsilon_1$, $\varepsilon_{air}$, $\varepsilon_{fluid}$. $V_{deflated}$, $\varepsilon_1$ may be deduced from other means of measurements and $\varepsilon_{air}$, $\varepsilon_{fluid}$ are known constants.

Thus, the above equation may be used to find $V_{fluid}$, for example using a numeric scheme.

It is expected that during the life of a patent maturing from this application many relevant methods and systems will be developed and the scope of the term a probe, a transducer, and an antenna is intended to include all such new technologies a priori.

As used herein the term "about" refers to ±10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A thoracic analysis device of deriving a total volume of fluids of a subject, comprising:
    a first interface for receiving a plurality of electromagnetic (EM) measurements of a plurality of EM signals, said plurality of EM signals are captured from a thoracic intrabody area of lungs of a subject in a plurality of different time points during a thoracic volume manipulation of said subject;
    a second interface for receiving a plurality of thoracic volume values, wherein each of said plurality of thoracic volume values is measured at one of said plurality of different time points during said thoracic volume manipulation of said subject; and
    a processor adapted to:
        deriving at least one individual thoracic parameter by combining between said plurality of EM measurements and said plurality of thoracic volume values;
        personalizing a dielectric model according to the at least one individual thoracic parameter;
        using said personalized dielectric model for calibrating a plurality of later EM measurements of a plurality of later EM signals captured by said first interface from the thoracic intrabody area of lungs of the subject; and
        calculating a total volume of fluids in the lung of the subject according to said plurality of calibrated EM measurements for a member of a group consisting of: tissue diagnosis, organ diagnosis, tissue monitoring, organ monitoring, organ performance assessment, tissue performance assessment and a medical decision aiding procedure.

2. The device of claim 1, wherein said second interface receives said plurality of thoracic volume values from an instrument for measuring at least one of a breathing airflow of said subject.

3. The device of claim 1, further comprising a presentation unit which presents instructions indicative of how to perform said thoracic volume manipulation in a correlated manner with the measurement of said plurality of thoracic volume values.

4. The device of claim 1, wherein said processor is configured to derive one or more clinical parameters according to the total volume.

5. A method using a processor for deriving a total volume of fluids of a subject, comprising:
    capturing a plurality of electromagnetic (EM) measurements of a plurality of EM signals, said plurality of EM signals are captured from a thoracic intrabody area of lungs of a subject at a plurality of different time points while said subject performs at least one thoracic volume manipulation;
    receiving a plurality of thoracic volume values measured at said plurality of different time points;

using said processor for executing software instructions for:
  deriving at least one individual thoracic parameter of said subject using said plurality of EM measurements and said plurality of thoracic volume values,
  personalizing a dielectric model according to the at least one individual thoracic parameter,
  using the personalized dielectric model for calibrating a plurality of later EM measurements of a plurality of later EM signals captured from the thoracic intrabody area of lungs of the subject, and
  calculating a total volume of fluids in the lung of the subject based on said plurality of calibrated EM measurements for a member of a group consisting of: tissue diagnosis, organ diagnosis, tissue monitoring, organ monitoring, organ performance assessment, tissue performance assessment and a medical decision aiding procedure.

6. The method of claim 5, wherein said plurality of thoracic volume values comprise at least a breathing value of said subject.

7. The method of claim 5, wherein said at least one individual thoracic parameter comprises a member of a group consisting of: heart dimension(s), heart position, fat layer dimensions, thoracic muscle dimension(s), thoracic rib dimension(s), thoracic rib position, lung volume, lung dimension(s), and thorax dimension(s).

8. The method of claim 5, wherein said at least one individual thoracic parameter comprises dielectric related properties of at least one of a thoracic tissue and a thoracic organ of said subject.

9. The method of claim 5, wherein said total volume is used to derive at least one clinical parameter of said subject.

10. The method of claim 9, wherein said at least one clinical parameter comprises a member of a group consisting of fluid and/or gas volume in the thorax and/or lung tissue, percentage of fluid in a lung tissue, parameters indicative of fluid content and/or content change, and/or percentage of fluid change in lung tissue.

11. The method of claim 5, wherein said plurality of EM signals pass through said lungs.

12. The method of claim 5, further comprising presenting to said subject breathing instructions for said subject to perform during said thoracic volume manipulation.

13. The method of claim 5, wherein said deriving at least one individual thoracic parameter is performed according to one or more demographic parameters relating to the subject.

14. The method of claim 5, wherein said deriving at least one individual thoracic parameter is performed according to a measured amplitude ratio between a transmitted signal and a received signal.

15. The method of claim 5, wherein said deriving at least one individual thoracic parameter comprises calculating a phase shift based on said plurality of EM measurements.

16. The method of claim 5, wherein said deriving at least one individual thoracic parameter comprises calculating fluid content of said lungs.

17. The method of claim 5, wherein said deriving at least one individual thoracic parameter comprises calculating a depth of said lungs.

* * * * *